(12) United States Patent
Davoodi et al.

(10) Patent No.: US 12,736,447 B2
(45) Date of Patent: Sep. 15, 2026

(54) APPARATUS AND METHOD FOR TESTING A DRILL CUTTINGS DISPERSION

(71) Applicant: Schlumberger Technology Corporation, Sugar Land, TX (US)

(72) Inventors: Mahdi Davoodi, Cambridge (GB); Evgeny Barmatov, Cambridge (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 273 days.

(21) Appl. No.: 18/733,961

(22) Filed: Jun. 5, 2024

(65) Prior Publication Data

US 2025/0377270 A1 Dec. 11, 2025

(51) Int. Cl.
*G01N 1/38* (2006.01)
*G01N 33/28* (2006.01)

(52) U.S. Cl.
CPC ........... *G01N 1/38* (2013.01); *G01N 33/2823* (2013.01); *G01N 2001/386* (2013.01)

(58) Field of Classification Search
CPC . G01N 1/38; G01N 33/2823; G01N 2001/386
USPC .......................................................... 73/64.56
See application file for complete search history.

(56) References Cited

U.S. PATENT DOCUMENTS 3,803,903 A * 4/1974 Lin ........................ G01N 11/14 73/54.28
2004/0255649 A1 12/2004 Zougari
2005/0170516 A1* 8/2005 Kharrat .............. G01N 33/2823 436/60
2015/0015104 A1* 1/2015 Kataoka ................. H02K 16/02 310/80
2017/0176310 A1* 6/2017 Jamison ................. G01N 11/14
2019/0068035 A1* 2/2019 Koizumi ................ H02K 16/00
2025/0377270 A1* 12/2025 Davoodi .................. G01N 1/38

FOREIGN PATENT DOCUMENTS

WO 2007033479 A1 3/2007

OTHER PUBLICATIONS

ASTM D4644-16, Standard Test Method for Slake Durability of Shales and Other Similar Weak Rocks, 2016, 4 pages.
Davoodi, Mahdi. Controlling purely elastic instabilities. The University of Liverpool, United Kingdom, 2019, 189 pages.
Du, H. et al., "Modelling the effect of mudstone cuttings on rheological properties of KCT/Polymer water-based drilling fluid", Journal of Petroleum Science and Engineering, 2018, 170, pp. 422-429.

* cited by examiner

*Primary Examiner* — Peter J Macchiarolo
*Assistant Examiner* — Rodney T Frank
(74) *Attorney, Agent, or Firm* — Kyle R. Miiller

(57) ABSTRACT

A method for evaluating a multiphase fluid includes adding the multiphase fluid to an annular volume of a test apparatus, the test apparatus including an inner cylinder deployed in an outer cylinder thereby defining the annular volume. The inner and outer cylinders are configured to rotate independently with respect to one another. The method further includes rotating at least one of the inner and outer cylinders after adding the multiphase fluid to the annular volume to simulate desired flow conditions in the annular volume. The method still further includes removing the multiphase fluid from the annular volume after rotating and evaluating at least one physical property of the removed multiphase fluid.

20 Claims, 3 Drawing Sheets

APPARATUS AND METHOD FOR TESTING A DRILL CUTTINGS DISPERSION

BACKGROUND

In subterranean drilling operations, such as for geothermal wells or for oil and gas exploration and production, drilling fluid is circulated in the wellbore while drilling. The drilling fluid performs many functions during a drilling operation, including flushing the cuttings away from the drill bit at the cutting interface, transporting the cuttings through the wellbore annulus to the surface, and providing for and enabling cuttings separation at the surface on shale shakers or other solids control equipment.

Formation solids that are generated by the drill bit (the cuttings) and other solids generated by well instability (e.g., washout) often contain clay minerals. These clay minerals may swell, erode, and/or disperse in circulating aqueous drilling fluids, which can in turn result in a reduction in size and hardness of the solids and further increase the difficulty of separating (removing) the solids from the drilling fluid. Residual formation solids in the drilling fluid can have a serious negative impact on drilling operations, for example, via increasing the density and viscosity of the drilling fluid which may in turn increase maintenance costs and necessitate increased dilution of the fluid.

One traditional method for reducing clay dispersion is the use of drilling fluids including salts and/or shale inhibitors. It is believed that organic shale inhibitor molecules adsorb onto clay surfaces competing with water molecules, thereby reducing clay swelling, erosion, and dispersion of the particles. One difficulty in formulating such drilling fluids and drilling fluid additives is that the swelling, erosion, and dispersion of the cuttings particles can be highly flow dependent (e.g., depend strongly on the flow conditions of the fluid in the wellbore). A dispersion test is commonly used in the industry to determine the effectiveness of salts, organic inhibitors, and other additives to inhibit dispersion of the cuttings particles. In one dispersion test, a clay sample is mixed with drilling fluid and hot rolled for 16 hours at 150 degrees F. (about 65 degrees C.). After hot rolling, the remaining cuttings are screened using a 20 mesh (0.841 mm) screen and then washed and dried to obtain the percentage recovered. While such dispersion testing may be useful, hot rolling will not accurately model the drilling fluid flow conditions found in the wellbore annulus and may therefore not provide an accurate indication of the effectiveness (or lack thereof) of a tested drilling fluid additive. There is a need in the industry for an improved apparatus and corresponding method for dispersion testing.

BRIEF DESCRIPTION OF THE DRAWINGS

For a more complete understanding of the disclosed subject matter, and advantages thereof, reference is now made to the following descriptions taken in conjunction with the accompanying drawings, in which.

DETAILED DESCRIPTION

Embodiments of this disclosure include apparatuses and methods for evaluating a multiphase fluid. One example apparatus includes an inner cylinder deployed in an outer cylinder, the deployment defining an annular volume between an outer surface of the inner cylinder and an inner surface of the outer cylinder. The inner and outer cylinders are configured to rotate independently with respect to one another. First and second end covers are deployed on opposing axial ends of the inner and outer cylinders. The first and second end covers are configured to seal the annular volume. A first motor is configured to rotate the inner cylinder with respect to the first and second end covers and a second motor is configured to rotate the outer cylinder with respect to the first and second end covers.

An example method includes adding the multiphase fluid to an annular volume of a test apparatus, the test apparatus including an inner cylinder deployed in an outer cylinder thereby defining the annular volume. The inner and outer cylinders are configured to rotate independently with respect to one another. The method further includes rotating at least one of the inner and outer cylinders after adding the multiphase fluid to the annular volume to simulate desired flow conditions in the annular volume. The method still further includes removing the multiphase fluid from the annular volume after rotating and evaluating at least one physical property of the removed multiphase fluid.

Figure 1:
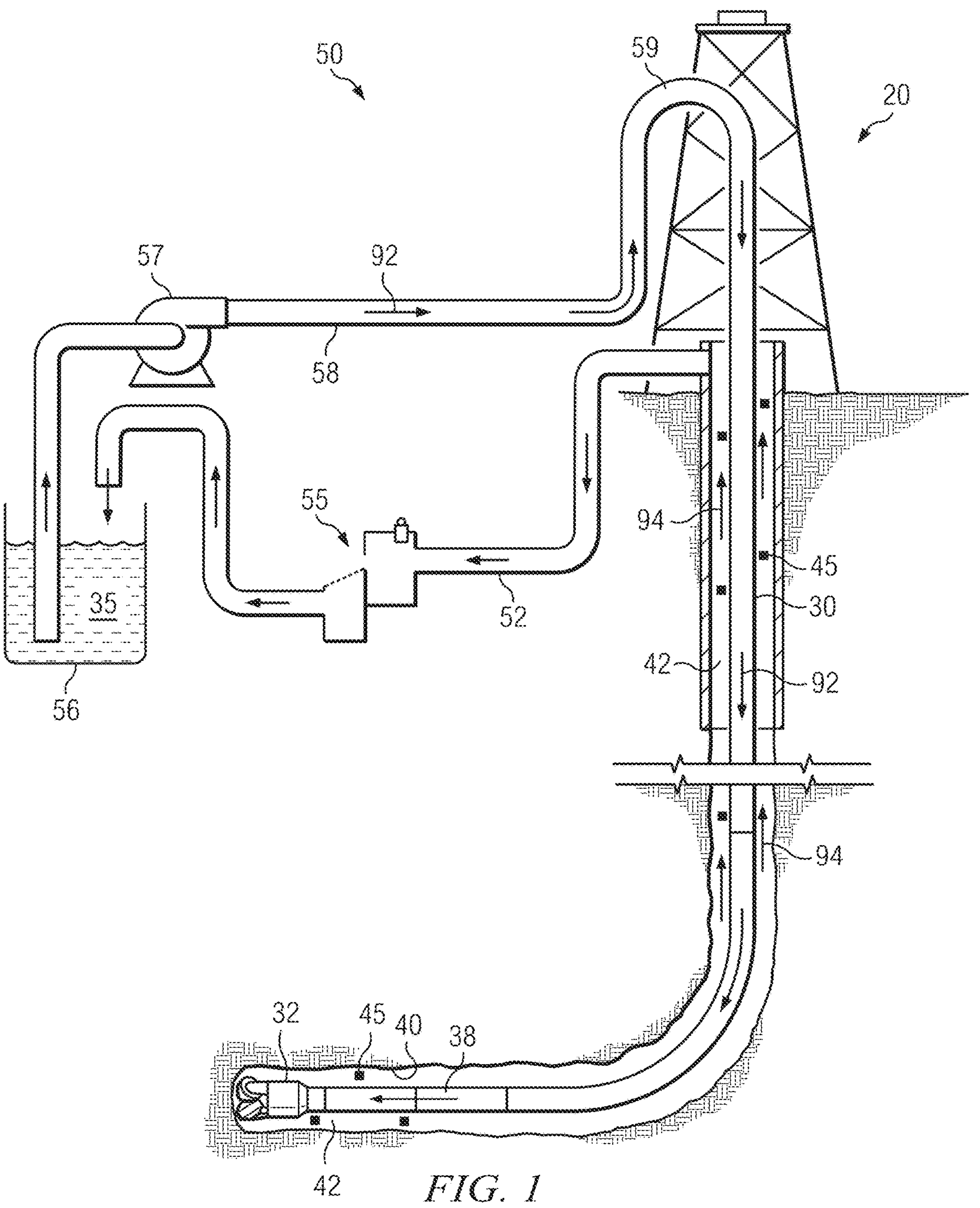
FIG. 1 depicts an example drilling rig.

FIG. 1 depicts an example drilling rig 20 positioned over a subterranean formation (not shown). The rig 20 may include, for example, a derrick and a hoisting apparatus (also not shown) for raising and lowering a drill string 30, which, as shown, extends into wellbore 40 and includes, for example, a drill bit 32 and one or more downhole measurement tools 38 (e.g., a logging while drilling tool or a measurement while drilling tool) in a bottom hole assembly (BHA) above the bit 32. Suitable drilling systems, for example, including drilling, steering, logging, and other downhole tools are well known in the art.

While FIG. 1 depicts a land rig 20, it will be appreciated that the disclosed embodiments are equally well suited for land rigs or offshore rigs. As is known to those of ordinary skill, offshore rigs commonly include a platform deployed atop a riser that extends from the sea floor to the surface. The drill string extends downward from the platform, through the riser, and into the wellbore through a blowout preventer (BOP) located on the sea floor. The disclosed embodiments are not limited in these regards.

Drilling rig 20 may further include a surface system 50 for controlling the flow of drilling fluid used on the rig (e.g., used in drilling the wellbore 40). In the example rig depicted, drilling fluid 35 is pumped downhole (as depicted at 92), for example, via a conventional mud pump 57. The drilling fluid 35 may be pumped, for example, through a standpipe 58 and mud hose 59 en route to the drill string 30. The drilling fluid 35 typically emerges from the drill string 30 at or near the drill bit 32 and creates an upward flow 94 of mud through the wellbore annulus 42 (the annular volume between the drill string and the wellbore wall). The drilling fluid 35 then flows through a return conduit 52 to a mud pit system 56 where it may be recirculated. It will be appreciated that the terms drilling fluid and mud are used synonymously herein.

As noted above in the Background Section, the circulating drilling fluid 35 is intended to perform many functions during a drilling operation, including flushing the cuttings 45 away from the drill bit at the cutting interface, transporting the cuttings 45 through the wellbore annulus 42 to the surface, and providing for and enabling cuttings separation at the surface. The drill cuttings 45 are commonly removed from the returning mud via a shale shaker 55 (or other similar solids control equipment) in the return conduit (e.g., immediately upstream of the mud pits 56). The drill cuttings 45 may be examined to evaluate properties of the subterranean formation layers through which the wellbore is drilled as is known to those of ordinary skill.

During rotary drilling operations, the drill string 30 rotates in the wellbore. Recommended drill string rotation rates for cuttings transport and hole cleaning generally depend on the diameters of the drill string and the wellbore as well as on the superficial flow velocity of the drilling fluid. Example best practices for common drill string and wellbore configurations often stipulate that a drill string rotation rate of greater than 100 rpm should be maintained for proper cuttings transport and hole cleaning. For such drilling operations and configurations, the drilling fluid may undergo complex Taylor vortex flow conditions with a superimposed axial flow. One aspect of the disclosed embodiments was the realization that the flow conditions in the wellbore may be simplified as a combination of two limiting flow conditions, a first flow condition resulting in simple shear owing to the axial flow of the drilling fluid and a second flow condition resulting in complex mixing in the presence of Taylor vortices owing to the rotation of the drill string.

Figures 2A, 2B, 3A, 3B:
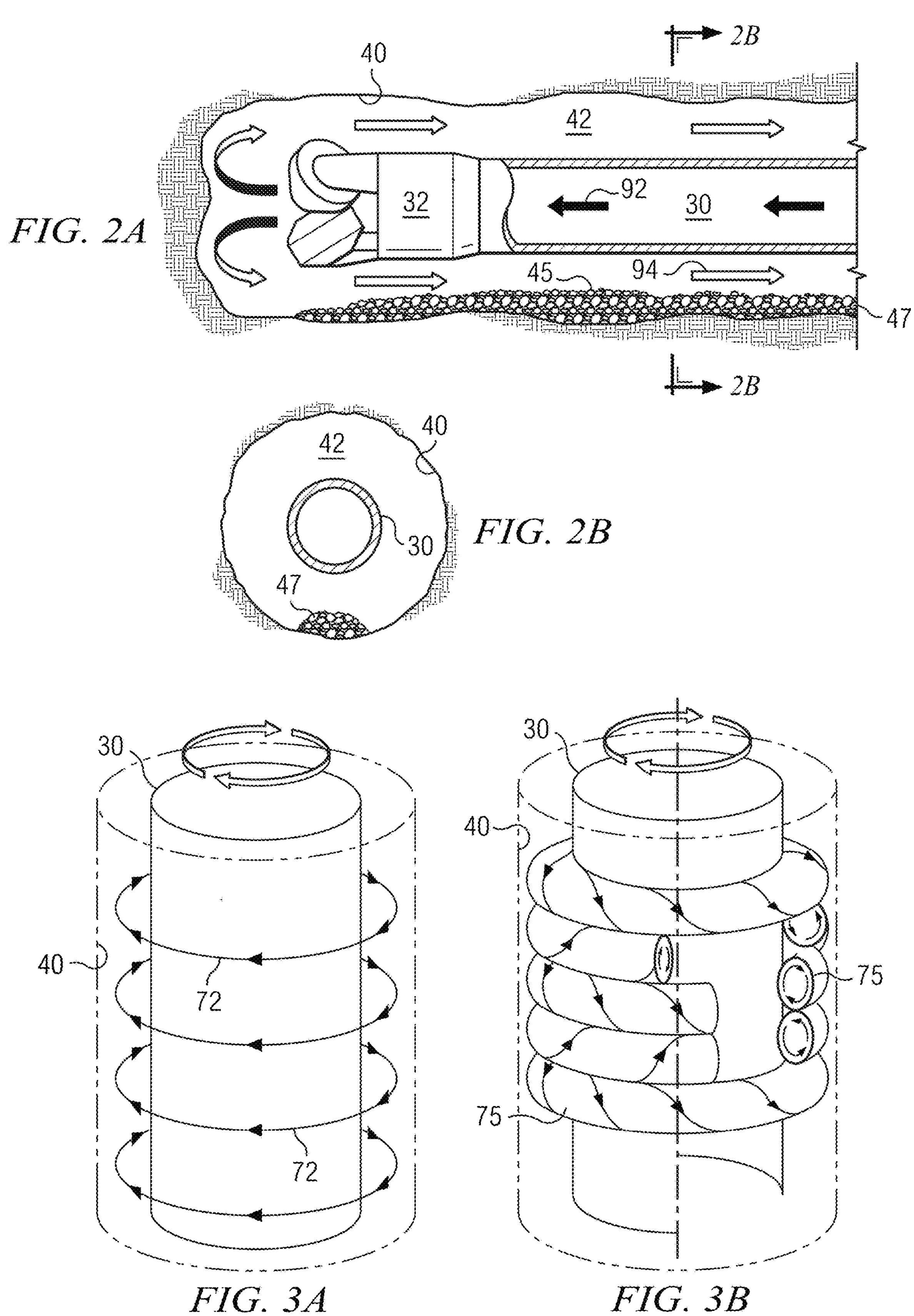
FIGS. 2A and 2B (collectively FIG. 2) depict a longitudinal cross section (FIG. 2A) and a circular cross section (FIG. 2B) of a drill string deployed in a horizontal section of wellbore.
FIGS. 3A and 3B (collectively FIG. 3) depict example flow conditions including curvilinear flow (3A) and Taylor vortices (3B).

FIGS. 2A and 2B (collectively FIG. 2) depict a longitudinal cross section (FIG. 2A) and a corresponding circular cross section (FIG. 2B) of a drill string 30 deployed in a horizontal section of wellbore 40. As also described above with respect to FIG. 1, the drilling fluid 35 flows towards the drill bit in the interior of the drill string 30 and towards the surface in the wellbore annulus 42. In the absence of any drill string rotation (the first flow condition noted above), the drilling fluid flow in the annulus 42 is generally subject to simple shear conditions owing to the axial flow 94 and can be estimated as axial flow inside an annulus (as depicted). In a long horizontal or near-horizontal section, in such fluid flow conditions, the cuttings 45 tend to sediment and form a bed on the lower side of the wellbore (as depicted collectively at 47). This bed tends to move slowly via saltation owing to drag and lift forces imposed by the shear rate.

FIGS. 3A and 3B (collectively FIG. 3) depict example flow conditions in the absence of axial flow (a drilling fluid flow rate approaching zero) and with drill string rotation (the second flow condition noted above). In FIG. 3A, the flow conditions are curvilinear as shown at 72 at low drill string rotation rates. In FIG. 3B the flow conditions become more complex with the presence of Taylor vortices as the drill string rotation rate increases. In the absence of axial flow, rotation of drill string 30 may lead to inertial instability at rotation rates above a critical rotation speed that leads to the presence of the Taylor vortices 75. Such vortices may be an effective mechanism to mix the surrounding fluid with the solid particles (such that the cuttings may remain mixed in the fluid rather than forming a sediment layer as shown on FIG. 2).

It will be appreciated that in common drilling operations, both drilling fluid circulation and drill string rotation are employed. The resulting drilling fluid flow conditions in the wellbore annulus may therefore include a complex flow pattern that is a mixture of axial flow (directed along the axis of the wellbore) induced by the circulating drilling fluid and curvilinear flow and/or rotational vortices induced by the rotating drill string. In the disclosed embodiments, a test apparatus is disclosed (and employed in corresponding test methods) that may advantageously enable flow conditions that are similar in flow type to those encountered downhole to be simulated and evaluated.

Figures 4, 5A, 5B, 5C, 6:
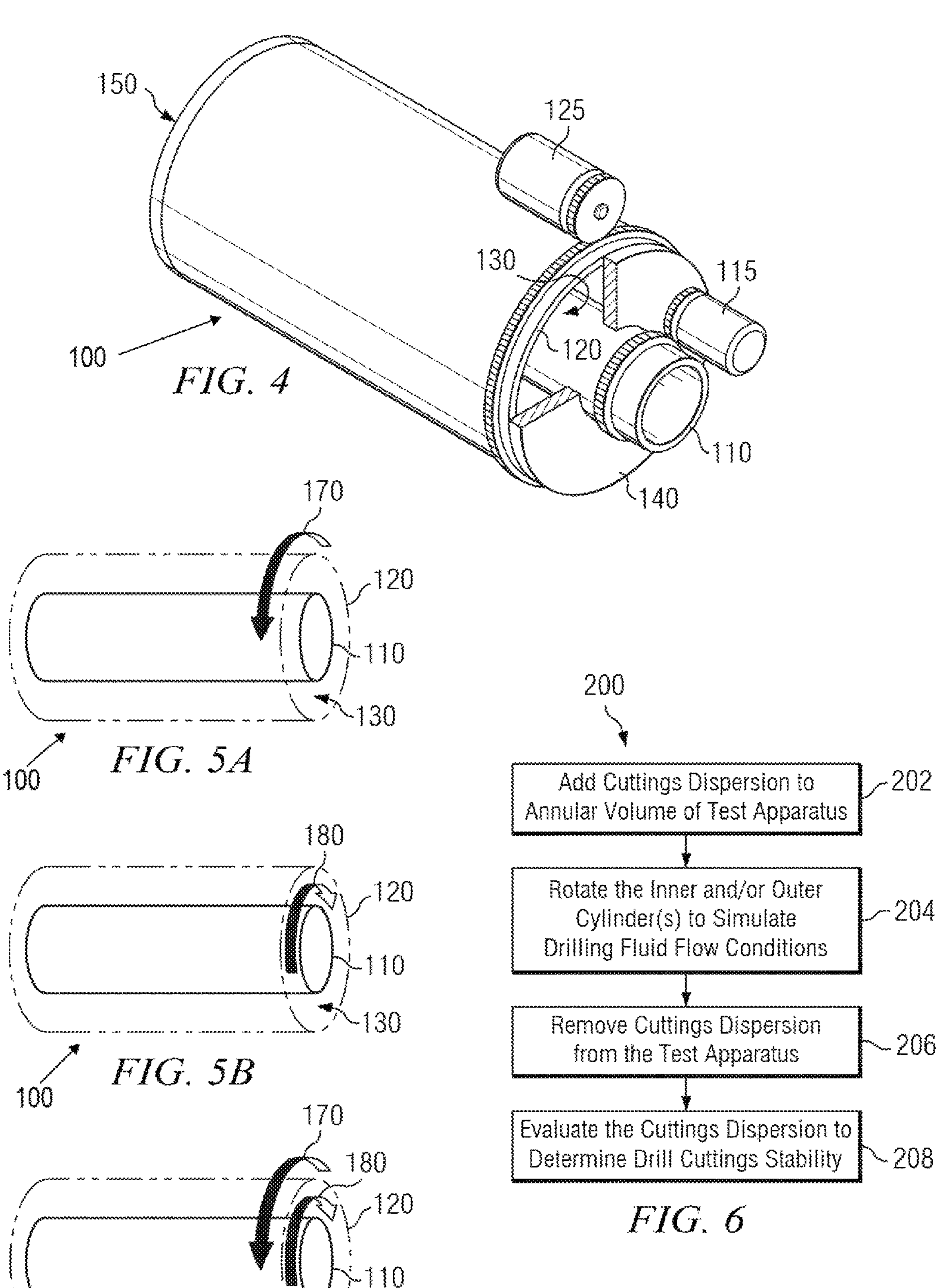
FIG. 4 depicts an example test apparatus disclosed herein.
FIGS. 5A, 5B, and 5C (collectively FIG. 5) depict example use cases of the test apparatus shown in FIG. 4 in which the outer cylinder is rotated (5A), the inner cylinder is rotated (5B), and both the outer and inner cylinders are rotated (5C).
FIG. 6 depicts a flowchart of one example disclosed method.

Turning now to FIG. 4, one example drilling fluid test apparatus is depicted. The depicted apparatus includes a first inner cylinder 110 deployed concentrically in a second outer cylinder 120 thereby defining an annular volume 130 between the inner and outer cylinders 110, 120. While the depicted embodiment illustrates concentric cylinders 110, 120, it will be appreciated that the disclosed embodiments are not limited in this regard. For example, eccentering the first cylinder in the second cylinder may enable downhole conditions to be evaluated (simulated) in which the drill string is eccentered in the wellbore (e.g. as is commonly encountered in horizontal or deviated wells). The apparatus further includes top 140 and bottom 150 end plates (or end covers) configured to retain and seal drilling fluid within the annular region 130. It will be appreciated that while the disclosed embodiments depict planar end covers 140, 150, that the disclosure is not so limited. For example, in certain embodiments it may be advantageous to use curved or conical end covers to reduce the influence of the covers on the flow conditions in the annulus.

With continued reference to FIG. 4, the inner and outer cylinders 110, 120 may be deployed or mounted on the end covers 140, 150 via the use of corresponding bearings (not shown) such that the cylinders may rotate independently with respect to the end covers. By rotate independently it is meant that rotation of each cylinder may be independently controlled. For example, the inner cylinder 110 may be rotated while the outer cylinder 120 remains stationary. Conversely, the inner cylinder 110 may remain stationary while the outer cylinder 120 may be rotated. Moreover, the inner cylinder 110 and the outer cylinder 120 may be rotated simultaneously in either the same direction or in opposite directions. As further depicted, the apparatus may include first and second motors (e.g., electrical motors) depicted schematically at 115 and 125 that are rotationally coupled to the first and second cylinders 110, 120. In such a configuration, the first electrical motor 115 is configured to rotate the first cylinder 110 and the second electrical motor 125 is configured to rotate the second cylinder 120.

In example embodiments, apparatus of FIG. 4, may be configured for use in a laboratory setting and may therefore be sized and shaped for operating in or on a confined space such as a bench top. While the disclosed embodiments are not limited to any particular dimensions, in such small-scale embodiments, the inner cylinder 110 may advantageously have a diameter, for example, in a range from about 4 cm to about 12 cm (e.g., about 8 cm) and the outer cylinder 120 may advantageously have a diameter, for example, in a range from about 8 cm to about 24 cm (e.g., about 16 cm). It will be appreciated that a diameter ratio of the outer cylinder to the inner cylinder may advantageously be similar to the diameter ratio of the wellbore to the drill string in a typical drilling operation (e.g., a ratio in a range from about 1.5 to about 3, such as a ratio of about 2). Moreover, in such small-scale embodiments, the overall length of each of the cylinders may be in a range from about 25 cm to about 100 cm (e.g., about 50 cm). It will be further appreciated that a ratio of the cylinder length to a diameter of the outer cylinder may advantageously be in a range from about 2 to about 4 (e.g., about 3) and that a ratio of the cylinder length to a diameter of the inner cylinder may advantageously be in a range from about 4 to about 8 (e.g., about 6). Moreover, a ratio of the cylinder length to the annular radius (the outer cylinder radius minus the inner cylinder radius) may be greater than about 3 (e.g., greater than about 4, or greater than about 5) to reduce the influence of the end covers on the flow conditions in the annulus.

The inner and outer cylinders 110, 120 and the end covers 140, 150 may be fabricated from substantially any suitable material. For example, the inner cylinder 110 may be fabricated from a similar steel to that of a drill string. Moreover, the outer cylinder 120 may include a textured inner surface intended to simulate the roughness of a borehole wall. In other embodiments, the outer cylinder 120 and/or one or both of the end covers 140, 150 may be fabricated from an optically transparent material (such as a clear plastic or glass) to enable a user to view the dispersion during use. Again, the disclosed embodiments are not limited in this regard.

While not shown on FIG. 4, it will be appreciated that the test apparatus may be configured to enable a user to readily add or remove a dispersion (such as a drilling fluid drill cuttings dispersion) to and from the annular volume 130. In example embodiments one or both of the covers 140, 150 may be configured to open and close thereby enabling the dispersion to be added to and removed from the annular volume. In an alternative embodiment, one or both of the covers 140, 150 may include a hatch (not shown) that is configured to open and close and thereby enable the dispersion to be added to and removed from the annular volume. In other example embodiments, the outer cylinder may include a sealable port that is configured to open and close and enable the dispersion to be added to and removed from the annular volume. It will be appreciated that the disclosed embodiments are not limited to any particular port or hatch structure or other suitable mechanism that enables the dispersion to be added to and removed from the annular volume.

With continued reference to FIG. 4, it will be appreciated that rotating the first and second cylinders 110, 120 at different rotational speeds (angular velocities) may enable different drilling fluid flow conditions to be simulated and tested. The first and second electrical motors 115, 125 may therefore advantageously be configured to provide variable rotation speeds such that the rotation speed of each cylinder may be independently adjusted/controlled over a wide range of speeds. In advantageous embodiments, the rotation speed of each cylinder may be independently adjusted over a wide range, for example, up to at least 100 rpm (e.g., up to at least 200 rpm, up to at least 400 rpm, up to at least 600 rpm, or up to at least 1000 rpm). It will be appreciated that the rotation speed required to induce Taylor vortices is generally inversely related to the size of the apparatus (e.g., to the annular radius) such that a smaller apparatus may require the use of higher speed motors.

While the disclosed embodiments are described herein with respect to a drill cuttings dispersion, it will be appreciated that the disclosed embodiments are not so limited. The disclosed apparatus in FIG. 4 may be employed to evaluate substantially any suitable multiphase fluid, such as a dispersion or mixture of solid particles in a liquid carrier or a multiphase liquid such as an emulsion. For example, apparatus of FIG. 4 may be employed to evaluate drag reducing agents in general and more particularly high molecular weight polymeric drag reducing agents dispersed in a water-based or oil-based liquid carrier. The apparatus of FIG. 4 may be further employed to evaluate emulsions such as are commonly employed in drilling fluids.

Turning now to FIGS. 5A, 5B, and 5C (collectively FIG. 5), the use of apparatus 100 of FIG. 4 to generate various flow conditions in the annulus 130 (FIG. 4) is described in more detail. In FIG. 5A, the outer cylinder 120 is rotated as shown at 170 while the inner cylinder 110 remains stationary to simulate pure or nearly pure shear flow conditions (the first flow condition described above). During a drilling process, the axial flow of drilling fluid in the annulus (in the absence of drill string rotation) may result in simple (nearly pure) shear flow conditions. Such flow conditions generally do not lead to complex flow and may be simulated using the simple curvilinear shear flow achieved through rotation of the outer cylinder 120 alone. Moreover, in this simulation increasing the rotation rate of the outer cylinder 120 advantageously simulates increasing drilling fluid flow rates (increasing axial flow) since complex flow instabilities do not tend to be introduced via rotation of the outer cylinder.

In a downhole drilling operation, the shear rate of the drilling fluid in a wellbore annulus $\dot{\gamma}_{dh}$ induced by circulating drilling fluid may be estimated, for example, as follows:

$$\dot{\gamma}_{dh} = \frac{U_a}{(R_h - r_{ds})} \tag{1}$$

where $U_a$ represents the average axial velocity of the drilling fluid in the wellbore annulus (which is related to the drilling fluid pump pressure at the surface in the wellbore and drill string geometry), $R_h - r_{ds}$ represents the annular radius, $R_h$ represents the radius of the wellbore, and $r_{ds}$ represents the radius of the drill string. It will be appreciated that the shear rate of the drilling fluid may be estimated for substantially any drilling operation using Eq. (1). As noted above, one advantage of the use of apparatus 100 is that the downhole flow conditions can be simulated in the test apparatus. For example, the shear rate $\dot{\gamma}_{lab}$ of drilling fluid in the test apparatus may be estimated, for example, as follows:

$$\dot{\gamma}_{lab} = \frac{R\omega_o}{(R - r)} \tag{2}$$

where R−r represents the annular radius of the test apparatus, R represents the inner radius of outer cylinder 120, r represents the outer radius of inner cylinder 110, and $\omega_o$ represents the angular rotation rate of the outer cylinder in units of radians per second. Note, that in Eq. (2), the shear rate of the drilling fluid is directly proportional to the rotation rate of the outer cylinder. Therefore, for a given test apparatus (having a fixed geometry) the rotation rate of the outer cylinder may be selected such that the shear rate of the drilling fluid in the test apparatus is equal to the shear rate of drilling fluid in a downhole drilling operation (e.g., such that $\dot{\gamma}_{lab} \approx \dot{\gamma}_{dh}$). Moreover, the rotation rate of the outer cylinder may be adjusted to simulate substantially any suitable range of shear rates found in a particular drilling operation (or set of operations).

Turning now to FIG. 5B, the inner cylinder 110 is rotated as shown at 180 while the outer cylinder 120 remains stationary to simulate complex mixing conditions including Taylor vortices when the rotation rate of the inner cylinder exceeds a critical speed (the second flow condition resulting described above). During a drilling operation, such vortices may be induced via rotation of the drill string (e.g., in the absence of or at low drilling fluid flow rates). Such flow conditions are not generally induced via rotation of the outer cylinder 120, but may be induced via rotating the inner cylinder 110 as described above. Moreover, in this simulation increasing the rotation rate of the inner cylinder 110 advantageously simulates the increasing shear and complex mixing induced by vortices via increasing the drill string rotation rate.

In a downhole drilling operation, the shear rate of the drilling fluid Yah induced by rotation of the drill string may be estimated, for example, as follows:

$$\dot{\gamma}_{dh} = \frac{r_{ds}\omega_{ds}}{(R_h - r_{ds})} \tag{3}$$

where $\omega_{ds}$ represents the angular rotation rate of the drill string in units of radians per second and $R_h$ and $r_{ds}$ are defined above. Moreover, the complex flow conditions in the wellbore, in the leading order of magnitude of the ratio of inertial force to viscous force may be scaled as a modified Taylor number, for example, as follows:

$$Ta_{dh} = \frac{\rho(r_{ds}\omega_{ds})(R_h - r_{ds})}{\eta(\dot{\gamma}_{dh})}\sqrt{\frac{(R_h - r_{ds})}{r_{ds}}} \tag{4}$$

where Tach represents the Taylor number of the complex flow conditions in the wellbore, p represents the density of the drilling fluid, and $\eta(\dot{\gamma}_{dh})$ represents the shear viscosity of the drilling fluid in the downhole environment. It will be appreciated that the drill string rotation induced shear and complex mixing may be estimated for substantially any drilling operation using Eqs. (3) and (4). As noted above, one advantage of the use of apparatus of FIG. 4 is that such downhole flow conditions can be simulated in the test apparatus. For example, the shear rate $\dot{\gamma}_{lab}$ of drilling fluid in the test apparatus may be estimated, for example, as follows:

$$\dot{\gamma}_{lab} = \frac{r\omega_i}{(R - r)} \tag{5}$$

where $\omega_i$ represents the angular rotation rate of the inner cylinder in units of radians per second and R and r are defined above with respect to Eq. (2). Moreover, the complex flow conditions in the wellbore may be scaled as a modified Taylor number, for example, as follows:

$$Ta_{lab} = \frac{\rho(r\omega_i)(R - r)}{\eta(\dot{\gamma}_{lab})}\sqrt{\frac{(R - r)}{r}} \tag{6}$$

where $Ta_{lab}$ represents the Taylor number of the complex flow conditions in the test apparatus, $\rho$ represents the density of the drilling fluid, and $\eta(\dot{\gamma}_{lab})$ represents the shear viscosity of the drilling fluid in the test apparatus. Note, that in Eqs. (5) and (6), the shear rate and the Taylor number of the drilling fluid is directly proportional to the rotation rate of the inner cylinder. Therefore, for a given test apparatus (having a fixed geometry) the rotation rate of the inner cylinder may be selected such that the shear rate of the drilling fluid in the test apparatus is about equal to the shear rate of drilling fluid in a downhole drilling operation (e.g., such that $\dot{\gamma}_{lab} \approx \dot{\gamma}_{dh}$) and/or such that the Taylor number of the drilling fluid in the test apparatus is about equal to the Taylor number of drilling fluid in the wellbore (e.g., such that $Ta_{lab} \approx Ta_{dh}$). Moreover, the rotation rate of the inner cylinder may be adjusted to simulate substantially any suitable range of shear rates and Taylor numbers found in a particular drilling operation (or set of operations).

In FIG. 5C, both the inner cylinder 110 and outer cylinder 120 are rotated (e.g., in opposite directions as depicted at 170, 180) to simulate general flow conditions including a mixture of the first and second flow conditions described above (e.g., ranging from simple shear to more complex flow conditions including both axial shear and Taylor vortices). During a drilling operation, such conditions are commonly encountered as drilling fluid is circulated and the drill string rotates in the wellbore. Moreover, in this simulation varying the rotation rates of the inner and outer cylinders (or varying a difference between the inner and outer rotation rates) may advantageously simulate the complex mixed shear and vortices flow conditions induced by both circulating drilling fluid and drill string rotation rate during a drilling operation.

In a downhole drilling operation, the shear rate of the drilling fluid $\dot{\gamma}_{dh}$ induced by circulating drilling fluid and rotation of the drill string may be estimated, for example, as follows:

$$\dot{\gamma}_{dh} = \frac{\sqrt{U_a^2 + (r_{ds}\omega_{ds})^2}}{(R_h - r_{ds})} \tag{7}$$

where $U_a$, $\omega_{ds}$, $R_h$ and $r_{ds}$ are defined above with respect to Eqs (1)-(6). Moreover, the Taylor number quantifying the complex flow conditions may again be given by Eq. (4).

It will be appreciated that the shear and complex mixing conditions induced by circulating drilling fluid and drill string rotation may be estimated for substantially any drilling operation using Eqs. (7) and (4). As noted above, one advantage of the use of the apparatus in FIG. 4 is that such downhole flow conditions can be simulated in the test apparatus. For example, the shear rate $\dot{\gamma}_{lab}$ of drilling fluid in the test apparatus may be estimated, for example, as follows:

$$\dot{\gamma}_{lab} = \frac{(r\omega_i - R\omega_o)}{(R - r)} \tag{8}$$

where $\omega_i$, $\omega_o$, R and r are defined above with respect to Eqs. (1)-(6). Moreover, the Taylor number quantifying the complex flow conditions may again be given by Eq. (6).

Therefore, for a given test apparatus (having a fixed geometry) the rotation rates of the inner and outer cylinders may be selected such that the shear rate of the drilling fluid in the test apparatus is about equal to the shear rate of drilling fluid in a downhole drilling operation (e.g., such that $\dot{\gamma}_{lab} \approx \dot{\gamma}_{dh}$) and/or such that the Taylor number of the drilling fluid in the test apparatus is about equal to the Taylor number of drilling fluid in the wellbore (e.g., such that $Ta_{lab} \approx Ta_{dh}$). Moreover, the rotation rate of the inner and outer cylinders may be adjusted to simulate substantially any suitable range of shear rates and Taylor numbers found in a particular drilling operation (or set of operations).

Turning now to FIG. 6, a flowchart of one example method 200 for evaluating a multiphase fluid including drill cuttings in a sample of drilling fluid is depicted. The method includes adding a dispersion to the annular volume of a test apparatus (such as test apparatus in FIG. 4) at 202. The dispersion may include a dispersion of drill cuttings or simulated drill cuttings such as clay particles in a volume of drilling fluid. In example embodiments, the dispersion may be added to the annular volume as a previously prepared dispersion (in which the drill cuttings or simulated drill cuttings are first mixed/dispersed in the drilling fluid and then added to the annular volume). In other embodiments the dispersion may be prepared in the annular volume, for example, by first adding the drilling fluid and then adding the drill cuttings or simulated drill cuttings or by first adding the cuttings or simulated drill cuttings and then adding the drilling fluid. Adding the dispersion may further include opening or otherwise removing one of the top or bottom covers 140, 150 of the test apparatus in FIG. 4 to provide access to the annular region 130 and then closing or redeploying the top or bottom cover to seal the drilling fluid therein.

With continued reference to FIG. 6, method 200 may further include mixing the dispersion in the annulus at 204 via rotating at least one of the inner and outer cylinders to simulate a drilling fluid flow condition. For example, as described above with respect to FIG. 5A, the outer cylinder 120 may be rotated to simulate axial shear conditions. In another example as described above with respect to FIG. 5B, the inner cylinder 110 may be rotated to simulate drill string rotation induced shear and Taylor vortices. In still another example as described above with respect to FIG. 5C, the inner and outer cylinders may be rotated in opposite directions to induce complex flow conditions including both axial shear and drill string induced shear and Taylor vortices. As also described above, the rotation rate(s) may be selected to simulate desired flow conditions. Moreover, the duration of the rotation in 204 may be selected to simulate an estimated travel time of drill cuttings traversing the wellbore from the drill bit to the surface (e.g., based upon a known drilling fluid flow rate and the measured depth of the well).

The dispersion may be removed from the test apparatus at 206 and evaluated at 208 to determine at least one physical property of the removed dispersion (e.g., to determine the stability of the drill cuttings or simulated drill cuttings in the drilling fluid). In one example embodiment, the removed dispersion may be passed through a sieve to separate solid drill cuttings or simulated drill cuttings having a size above a predetermined threshold from the liquid. The separated material may be quantified (e.g., weighed) and compared with the quantity of drill cuttings or simulated drill cuttings added to the original dispersion. The separated material may alternatively and/or additionally be pressed in an extruder to estimate a bulk hardness of the cuttings after circulation in the fluid. The separated material may alternatively and/or additionally be dried to measure a moisture or hydration content of the drill cuttings (often referred to in the industry as a shale hydration).

Although not shown on FIG. 6, it will be appreciated that method 200 may further include modeling expected drilling fluid flow conditions in a wellbore, for example using one or more of Eqs. (1), (3), (4), and (7). The modeling may include, for example, evaluating selected variables from among the wellbore diameter, the drill string diameter, and the rotation rate of the drill string to model a drilling fluid shear rate in the wellbore. The modeling may further include, for example, evaluating selected variables from among the diameter of the wellbore, the diameter of the drill string, the drill string rotation rate, the density of the drilling fluid, and the shear viscosity of the drilling fluid in the wellbore to model Taylor vortices in the wellbore. In such embodiments, the rotation rates of the inner and outer cylinders may be selected such that the flow conditions in the test apparatus simulate the modeled downhole flow conditions.

It will be understood that the present disclosure includes numerous embodiments. These embodiments include, but are not limited to, the following embodiments.

In a first embodiment, an apparatus for evaluating a multiphase fluid comprises an inner cylinder deployed in an outer cylinder, the deployment defining an annular volume between an outer surface of the inner cylinder and an inner surface of the outer cylinder; first and second end covers deployed on opposing axial ends of the inner and outer cylinders, the first and second covers configured to seal the annular volume; a first motor configured to rotate the inner cylinder with respect to the first and second end covers; a second motor configured to rotate the outer cylinder with respect to the first and second end covers; and wherein the inner and outer cylinders are configured to rotate independently with respect to one another.

A second embodiment may include the first embodiment, wherein the inner cylinder is deployed coaxially in the outer cylinder.

A third embodiment may include any one of the first through second embodiments, wherein at least one of the first and second covers is configured to open and close thereby enabling the multiphase fluid to be added to and removed from the annular volume.

A fourth embodiment may include any one of the first through third embodiments, wherein the outer cylinder comprises a sealable port configured to enable the multiphase fluid to be added to and removed from the annular volume.

A fifth embodiment may include any one of the first through fourth embodiments, wherein the first and second motors comprise first and second electrical motors.

A sixth embodiment may include any one of the first through fifth embodiments, wherein a ratio of a diameter of the outer cylinder to a diameter of the inner cylinder is in a range from about 1.5 to about 3.

A seventh embodiment may include any one of the first through sixth embodiments, wherein a ratio of a length of the outer cylinder to an annular radius is greater than about 3.

An eighth embodiment may include any one of the first through seventh embodiments, wherein the inner cylinder has a diameter in a range from about 4 cm to about 12 cm; the outer cylinder has a diameter in a range from about 8 cm to about 24 cm; and the inner and outer cylinders have equal lengths in a range from about 25 to about 100 cm.

A ninth embodiment may include any one of the first through eighth embodiments, wherein the first and second motors are configured to rotate the corresponding inner and outer cylinders at rotation rates up to at least 100 rpm.

A tenth embodiment may include any one of the first through ninth embodiments, wherein at least one of the outer cylinder and the first and second end covers is optically transparent.

In an eleventh embodiment, a method for evaluating a multiphase fluid comprises adding the multiphase fluid to an annular volume of a test apparatus, the test apparatus including an inner cylinder deployed in an outer cylinder thereby defining the annular volume, the inner and outer cylinders being configured to rotate independently with respect to one another; rotating at least one of the inner and outer cylinders after adding the multiphase fluid to the annular volume to simulate desired flow conditions in the annular volume; removing the multiphase fluid from the annular volume after said rotating; and evaluating at least one physical property of the removed multiphase fluid.

A twelfth embodiment may include the eleventh embodiment, wherein the multiphase fluid is a dispersion of drill cuttings in a volume of drilling fluid.

A thirteenth embodiment may include any one of the eleventh through twelfth embodiments, wherein the rotating comprises rotating the outer cylinder to simulate axial shear induced by a flow of drilling fluid in a wellbore.

A fourteenth embodiment may include any one of the eleventh through twelfth embodiments, wherein the rotating comprises rotating the inner cylinder at a rotation rate below a threshold to simulate shear induced by rotation of a drill string in a wellbore.

A fifteenth embodiment may include any one of the eleventh through twelfth embodiments, wherein the rotating comprises rotating the inner cylinder at a rotation rate above a threshold to simulate mixed flow conditions including shear and Taylor vortices induced by rotation of a drill string in a wellbore.

A sixteenth embodiment may include any one of the eleventh through twelfth embodiments, wherein the rotating comprises rotating the inner cylinder and the outer cylinder in opposite directions to simulate complex flow conditions including shear induced by a flow of drilling fluid in a wellbore and shear and Taylor vortices induced by rotation of a drill string in a wellbore.

A seventeenth embodiment may include any one of the eleventh through sixteenth embodiments, further comprising modeling drilling fluid flow conditions in a wellbore; and wherein the rotating comprises selecting a rotation rate or rotation rates of the at least one of the inner and outer cylinders to simulate the modeled drilling fluid flow conditions in the wellbore.

An eighteenth embodiment may include the seventeenth embodiment, wherein the modeling drilling fluid flow conditions comprises evaluating selected ones of a wellbore diameter, a drill string diameter, and a rotation rate of a drill string to model a drilling fluid shear rate in the wellbore.

A nineteenth embodiment may include any one of the seventeenth through eighteenth embodiments, wherein the modeling drilling fluid flow conditions comprises evaluating selected ones of a diameter of a wellbore, a diameter of a drill string, a drill string rotation rate, a density of the drilling fluid, and a shear viscosity of the drilling fluid in the wellbore to model Taylor vortices in the wellbore.

A twentieth embodiment may include any one of the eleventh through nineteenth embodiments, wherein the evaluating further comprises passing the removed multiphase fluid through a sieve to separate solids having a size above a predetermined threshold; and at least one of the following: comparing a mass of the separated solids with a mass of solids added to the dispersion prior to the adding the dispersion to the annular volume; pressing the separated solids in an extruder to estimate a bulk hardness of the separated solids; and drying the separated solids to estimate a hydration content of the separated solids.

Although an apparatus and method for testing a drill cuttings dispersion has been described in detail, it should be understood that various changes, substitutions and alterations can be made herein without departing from the spirit and scope of the disclosure as defined by the appended claims.

The invention claimed is:

1. An apparatus for evaluating a multiphase fluid, the apparatus comprising:

an inner cylinder deployed in an outer cylinder, the deployment defining an annular volume between an outer surface of the inner cylinder and an inner surface of the outer cylinder;

first and second end covers deployed on opposing axial ends of the inner and outer cylinders, the first and second covers configured to seal the annular volume;

a first motor configured to rotate the inner cylinder with respect to the first and second end covers; and a second motor configured to rotate the outer cylinder with respect to the first and second end covers, wherein the inner and outer cylinders are configured to rotate independently with respect to one another.

2. The apparatus of claim 1, wherein the inner cylinder is deployed coaxially in the outer cylinder.

3. The apparatus of claim 1, wherein at least one of the first and second covers is configured to open and close thereby enabling the multiphase fluid to be added to and removed from the annular volume.

4. The apparatus of claim 1, wherein the outer cylinder comprises a sealable port configured to enable the multiphase fluid to be added to and removed from the annular volume.

5. The apparatus of claim 1, wherein the first and second motors comprise first and second electrical motors.

6. The apparatus of claim 1, wherein a ratio of a diameter of the outer cylinder to a diameter of the inner cylinder is in a range from about 1.5 to about 3.

7. The apparatus of claim 1, wherein a ratio of a length of the outer cylinder to an annular radius is greater than about 3.

8. The apparatus of claim 1, wherein:

the inner cylinder has a diameter in a range from about 4 cm to about 12 cm;

the outer cylinder has a diameter in a range from about 8 cm to about 24 cm; and the inner and outer cylinders have equal lengths in a range from about 25 to about 100 cm.

9. The apparatus of claim 1, wherein the first and second motors are configured to rotate the corresponding inner and outer cylinders at rotation rates up to at least 100 rpm.

10. The apparatus of claim 1, wherein at least one of the outer cylinder and the first and second end covers is optically transparent.

11. A method for evaluating a multiphase fluid, the method comprising:

adding the multiphase fluid to an annular volume of a test apparatus, the test apparatus including an inner cylinder deployed in an outer cylinder thereby defining the annular volume, the inner and outer cylinders being configured to rotate independently with respect to one another;

rotating at least one of the inner and outer cylinders after adding the multiphase fluid to the annular volume to simulate desired flow conditions in the annular volume;

removing the multiphase fluid from the annular volume after said rotating; and evaluating at least one physical property of the removed multiphase fluid.

12. The method of claim 11, wherein the multiphase fluid is a dispersion of drill cuttings in a volume of drilling fluid.

13. The method of claim 11, wherein the rotating comprises rotating the outer cylinder to simulate axial shear induced by a flow of drilling fluid in a wellbore.

14. The method of claim 11, wherein the rotating comprises rotating the inner cylinder at a rotation rate below a threshold to simulate shear induced by rotation of a drill string in a wellbore.

15. The method of claim 11, wherein the rotating comprises rotating the inner cylinder at a rotation rate above a threshold to simulate mixed flow conditions including shear and Taylor vortices induced by rotation of a drill string in a wellbore.

16. The method of claim 11, wherein the rotating comprises rotating the inner cylinder and the outer cylinder in opposite directions to simulate complex flow conditions including shear induced by a flow of drilling fluid in a wellbore and shear and Taylor vortices induced by rotation of a drill string in a wellbore.

17. The method of claim 11, further comprising modeling drilling fluid flow conditions in a wellbore; and wherein the rotating comprises selecting a rotation rate or rotation rates of the at least one of the inner and outer cylinders to simulate the modeled drilling fluid flow conditions in the wellbore.

18. The method of claim 17, wherein the modeling drilling fluid flow conditions comprises evaluating selected ones of a wellbore diameter, a drill string diameter, and a rotation rate of a drill string to model a drilling fluid shear rate in the wellbore.

19. The method of claim 17, wherein the modeling drilling fluid flow conditions comprises evaluating selected ones of a diameter of a wellbore, a diameter of a drill string, a drill string rotation rate, a density of the drilling fluid, and a shear viscosity of the drilling fluid in the wellbore to model Taylor vortices in the wellbore.

20. The method of claim 11, wherein the evaluating further comprises passing the removed multiphase fluid through a sieve to separate solids having a size above a predetermined threshold; and at least one of the following:

comparing a mass of the separated solids with a mass of solids added to the multiphase fluid prior to the adding the multiphase fluid to the annular volume;

pressing the separated solids in an extruder to estimate a bulk hardness of the separated solids; and drying the separated solids to estimate a hydration content of the separated solids.

* * * * *